United States Patent [19]
Wagener et al.

[11] Patent Number: 5,847,064
[45] Date of Patent: Dec. 8, 1998

[54] POLYCARBOMETALLANES VIA ACYCLIC DIENE METATHESIS POLYMERIZATION

[75] Inventors: Kenneth B. Wagener; Patrick S. Wolfe; Fernando J. Gómez, all of Gainesville, Fla.

[73] Assignee: University of Florida, Gainesville, Fla.

[21] Appl. No.: 807,494

[22] Filed: Feb. 27, 1997

[51] Int. Cl.[6] ............................................. C08F 30/04
[52] U.S. Cl. ........................... 526/335; 526/90; 526/159; 526/160; 526/221; 526/240; 526/241; 528/395
[58] Field of Search ............................. 528/395; 526/90, 526/159, 160, 221, 240, 241, 335

[56] References Cited

U.S. PATENT DOCUMENTS

| | | |
|---|---|---|
| 3,699,138 | 10/1972 | Debreczeni et al. . |
| 4,221,811 | 9/1980 | Bulten . |
| 4,282,165 | 8/1981 | Liauw et al. . |
| 4,943,397 | 7/1990 | Johnson . |
| 5,055,499 | 10/1991 | Endo et al. . |
| 5,589,548 | 12/1996 | Nubel et al. . |
| 5,597,875 | 1/1997 | Harwood et al. . |

OTHER PUBLICATIONS

F. Quignard, et al., "Aryloxide Ligands in the Metathesis of Olefins: Syntheses of W(OAr)$_x$Cl$_{6-x}$ Complexes with x=2, 3, and 4. Crystal Structures of W(O–2,6–C$_6$H$_3$–i–Pr$_2$)$_3$Cl$_3$ and W(O–2,6–C$_6$H$_3$Ph$_2$)$_2$Cl$_4$", *Inorg. Chem.* 26(25):4272–4277, 1987.

R.R. Schrock, et al., "Synthesis of Molybdenum Imido Alkylidene Complexes and Some Reactions Involving Acyclic Olefins", *J. Am. Chem. Soc.* 112 (10):3875–3886, 1990.

K.B. Wagener, et al., "Acyclic Diene Metathesis (ADMET) Polymerization", *Macromolecules* 24(10):2649–2657, 1991.

K.B. Wagener, et al., "The key to successful acyclic diene metathesis polymerization chemistry", *Makromol. Chem.* 191:365–374, 1990.

K. Brzezinska, et al., "Acyclic diene metathesis (ADMET) polymerization using a well–defined ruthenium based metathesis catalyst", *Macromol. Chem. Phys.* 197:2065–2074, 1996.

F.J. Goméz and K.B. Wagener, "ADMET polymerization using Classical Catalytic Systems", *Poly. Mats. Sci. & Eng.* 76:59, 1997.

P.O. Nubel, et al., "Acyclic Diene Metathesis Polymerization Using a Modified WCl$_6$–SnR$_4$ Olefin Metathesis Catalyst", *Macromolecules* 27(23):7000–7002, 1994.

W.A. Nugent, et al., "Practical Catalyst for Cyclic Metathesis. Synthesis of Functional and/or Enantiopure Cycloalkenes", *J. Am. Chem. Soc.* 117(35):8992–8998, 1995.

F. Quignard, et al., "Aryloxide Ligands in Metathesis of Olefins and Olefinic Esters: Catalytic Behaviour of W(OAr)$_2$Cl$_4$ Complexes Associated with Alkyl–Tin or Alkyl–Lead Cocatalysts; Alkylation of W(OAr)$_2$Cl$_4$ by SnMe$_4$, Sn(n–Bu)$_4$, Pb(n–Bu)$_4$, MgNp$_2$: Synthesis of W(OAr)$_2$Cl$_2$(CHCMe$_3$)(OR$_2$) and W(OAr)$_2$Cl(CHCMe$_3$)(CH$_2$CMe$_3$)(OR$_2$)", *J. Mol. Catalysis* 36:13–29, 1986.

*Primary Examiner*—John M. Cooney, Jr.
*Attorney, Agent, or Firm*—Quarles & Brady

[57] ABSTRACT

An organometallic polymer having the following moiety:

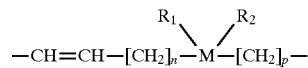

is disclosed. $R_1$ and $R_2$ are independently selected from the group of H, alkyl having 30 or fewer carbons, alkenyl having 30 or fewer carbons, and aromatic having one to ten rings; n=0–30; p=0–30; and M is a metal selected from the group consisting of Sn, Ge, Pb, Hg, Ni, Pd, Pt, Cr, Fe, Co, Cu, and Zn. Most preferably, M is Sn, $R_1$ and $R_2$ are n-butyl, n is 3, and p is 3. A preferred antibacterial/antifungal composition may be formed by combining the polymer with a suitable carrier.

13 Claims, 5 Drawing Sheets

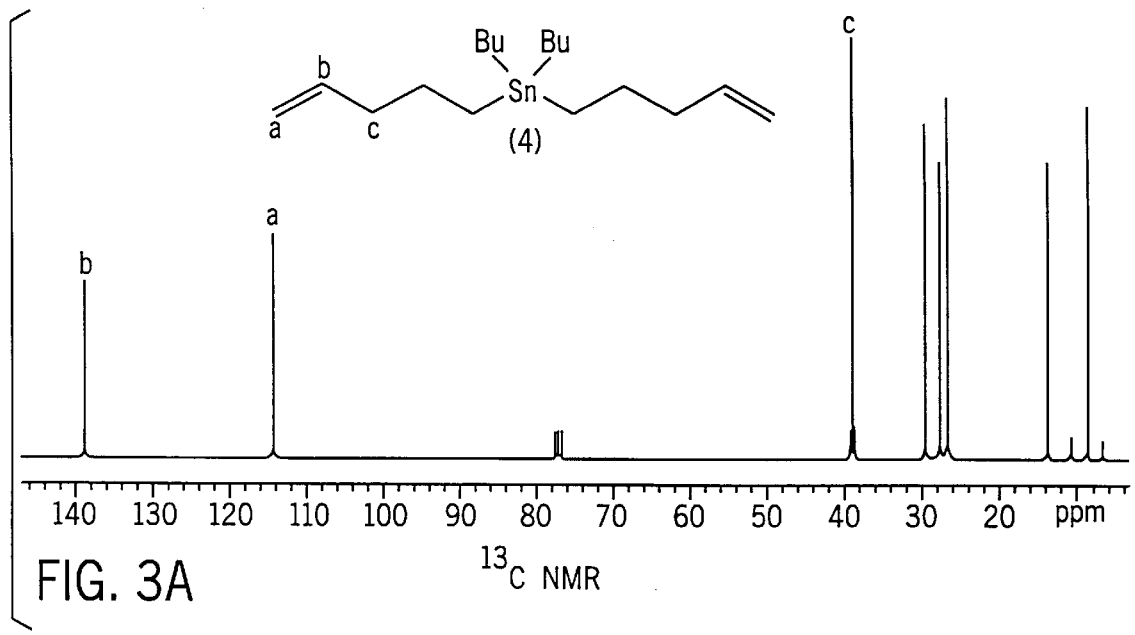
FIG. 3A    $^{13}$C NMR
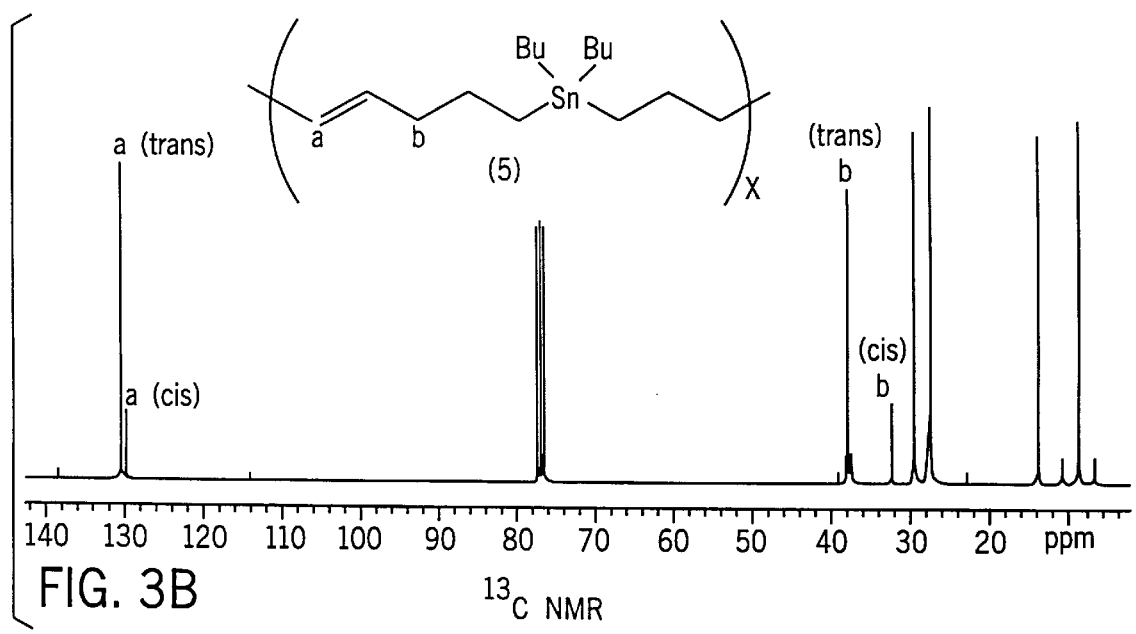
FIG. 3B    $^{13}$C NMR

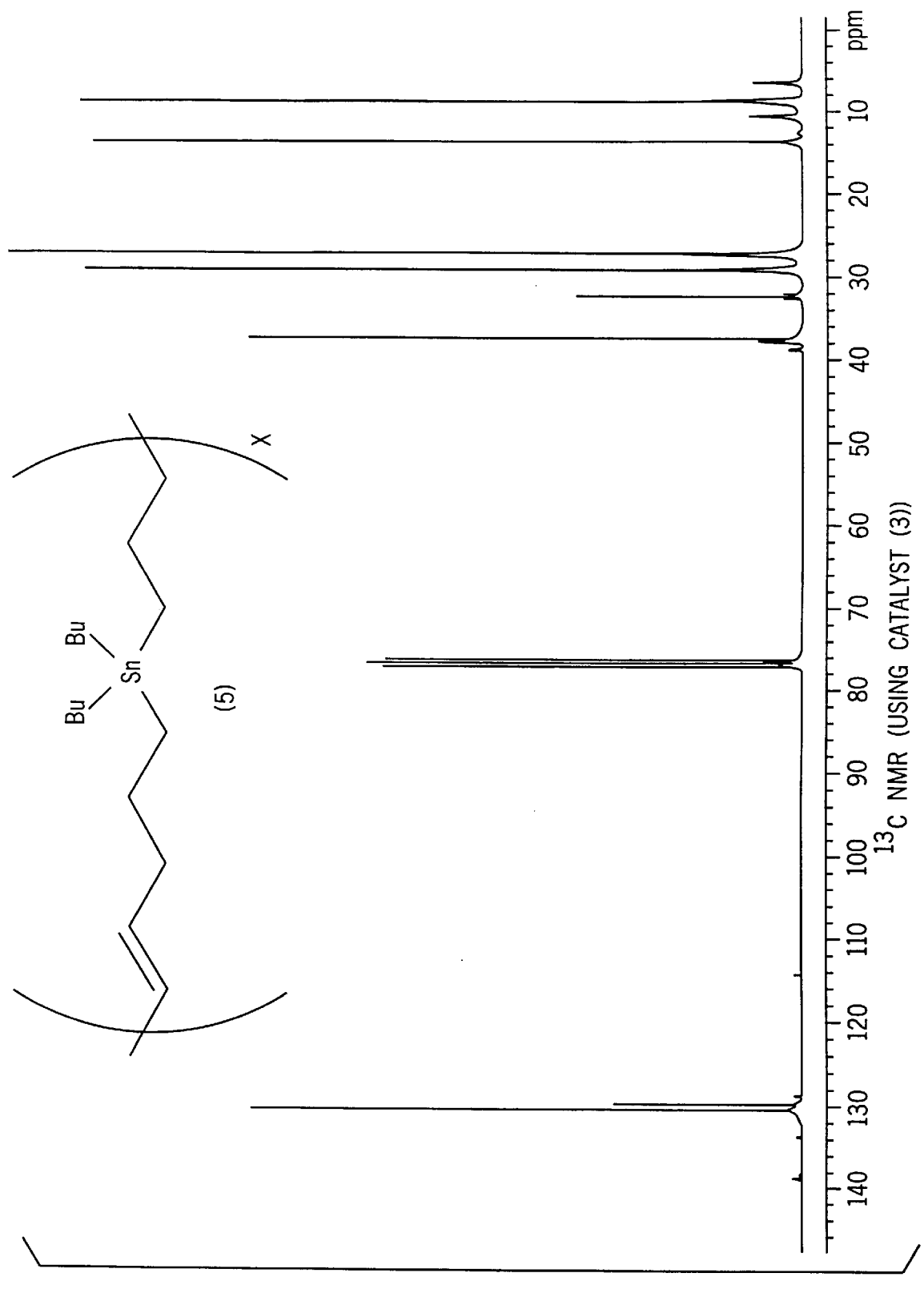

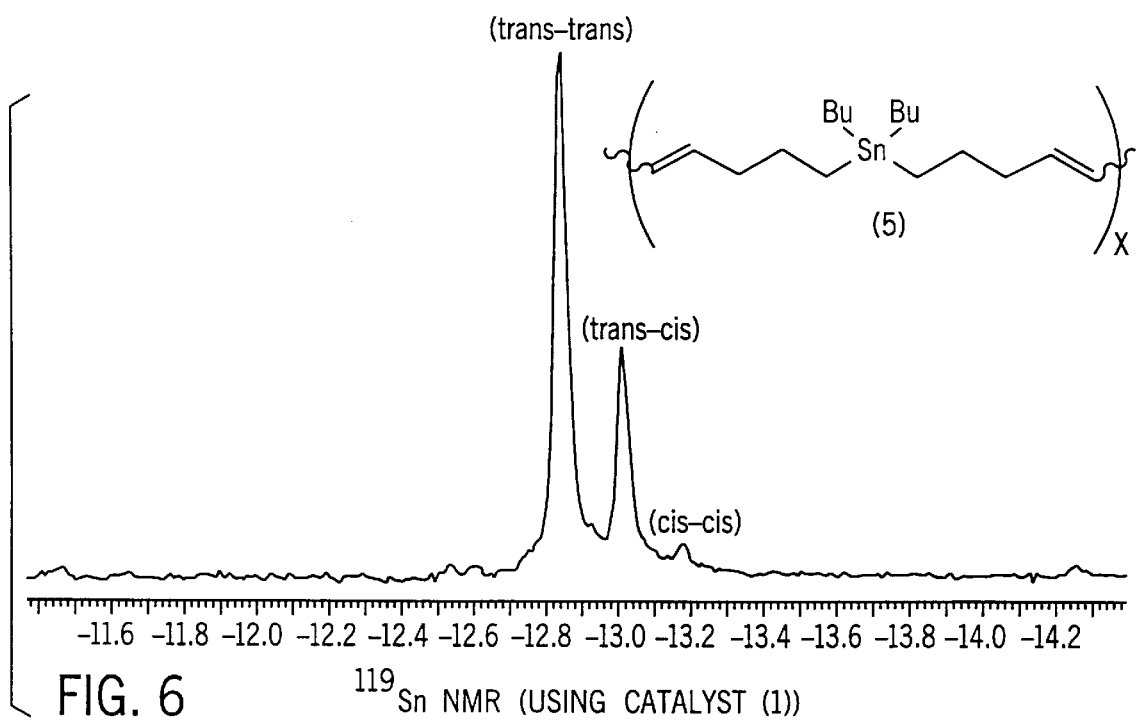
FIG. 6   $^{119}$Sn NMR (USING CATALYST (1))

POLYCARBOMETALLANES VIA ACYCLIC DIENE METATHESIS POLYMERIZATION

STATEMENT REGARDING FEDERALLY SPONSORED RESEARCH

This invention was made with United States Government support awarded by the National Science Foundation, Division of Materials Research, Grant No. DMR 9520803. The United States Government has certain rights in this invention.

CROSS REFERENCE TO RELATED APPLICATIONS

Not applicable.

BACKGROUND OF THE INVENTION

1. Field Of The Invention

This invention relates generally to polymers having antibacterial and antifungal properties. More particularly, it relates to polycarbometallanes and methods of making them.

2. Background of the Art

Previously, Basset and coworkers demonstrated that tungsten aryloxo complexes (i.e. (3) in FIG. 1) could efficiently catalyze the metathesis of cis-2-pentene in the presence of tetralkyltin or tetraalkyllead cocatalysts.[1] These observations were followed by the synthesis of cycloolefins by Feldman and coworkers utilizing the aryloxo tungsten complex (i.e. (2) in FIG. 1) in the presence of tetraethyllead.[2] Recently, Nubel and coworkers have shown that polybutadiene can be produced via acyclic diene metathesis ADMET condensation chemistry using $WCl_6/Me_4Sn$ in the presence of propyl acetate.[3] The disclosure of all the above articles, and of all other articles and patents cited herein, are incorporated by reference as if fully set forth herein.

SUMMARY OF THE INVENTION

We have discovered a new class of organometallic polymers which have antifungal and antibacterial properties. These polymers can be mixed with suitable carriers to make useful and economical compositions.

In one aspect, the invention provides an organometallic polymer having the following moiety:

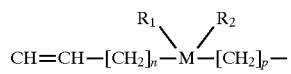

wherein n=0–30; p=0–30; $R_1$ and $R_2$ are independently selected from the group of H, alkyl having 30 or fewer carbons, alkenyl having 30 or fewer carbons, and aromatic having one to ten rings; and M is a metal selected from the group consisting of Sn, Ge, Pb, Hg, Ni, Pd, Pt, Cr, Fe, Co, Cu, and Zn. Most preferably, M is Sn, $R_1$ and $R_2$ are n-butyl, n is 3, and p is 3.

Another aspect of the invention provides an antibacterial, antifungal composition comprising polymers of the above kind and a suitable carrier.

A still further aspect of the invention provides a method of making an organometallic polymer comprising the steps of adding a bis(alkenyl) metal monomer to a suitable catalyst, but without the presence of co-catalyst; reacting the monomer under vacuum at a temperature between room temperature and 90° C. to form a crude mixture of a polymer having the moiety

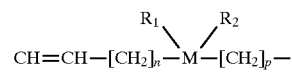

and purifying the polymer from the crude mixture; wherein n=0–30; p=0–30; $R_1$ and $R_2$ are independently selected from the group of H, alkyl having 30 or fewer carbons, alkenyl having 30 or fewer carbons, and aromatic having one to ten rings; and M is a metal selected from the group consisting of Sn, Ge, Pb, Hg, Ni, Pd, Pt, Cr, Fe, Co, Cu, and Zn. Preferably, the catalyst is selected from the group of molybdenum alkylidene and tungsten aryloxo complexes. It is also most preferred that M is Sn, $R_1$ and $R_2$ are n-butyl, n is 3, and p is 3.

Still another aspect of the invention provides a method of controlling the growth of organisms comprising contacting the organisms with compounds and compositions of the above kind in an amount effective for the control of the growth of the organisms.

These polymers (particularly those containing tin) are useful in antibacterial and antifungal coatings/compositions that can be used on the linings of ship hulls. Such coatings suppress the formation of barnacles and decrease hull drag.

The objects of the invention, therefore, include providing polymers and compositions of the above kind:

(a) which possess useful antibacterial and antifungal properties;

(b) which can be synthesized efficiently and at relatively low cost; and (c) which can be mixed with inexpensive carriers.

These and still other objects and advantages of the present invention will be apparent from the description below. However, this description is only of the preferred embodiments. The claims should, therefore, be looked to in order to assess the whole scope of the invention.

BRIEF DESCRIPTION OF THE DRAWINGS

FIGS. 3–6 show NMR's of various polymers of the present invention.

DETAILED DESCRIPTION OF THE INVENTION

Figure 1:
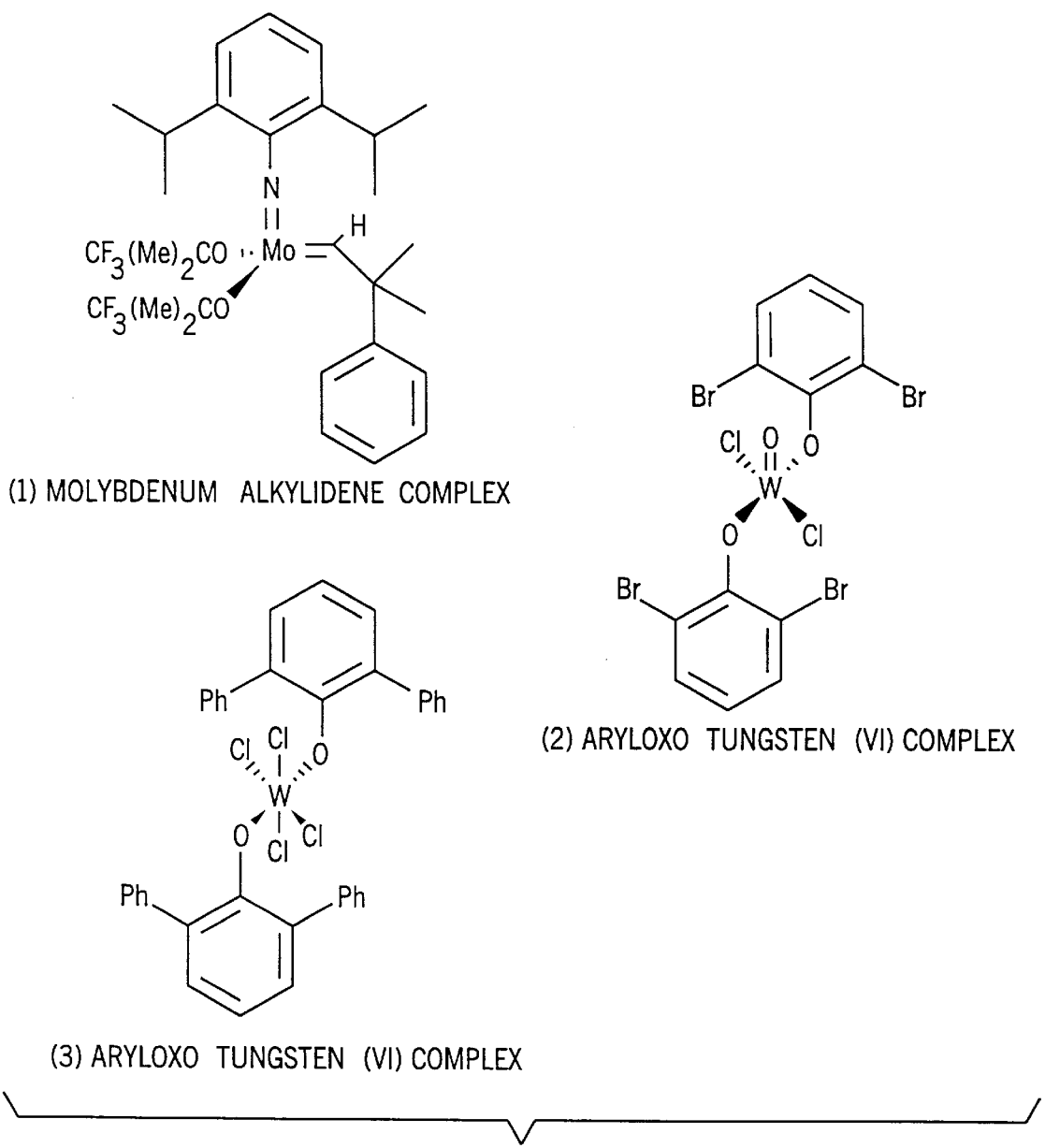
FIG. 1 shows the structure of various catalysts of the present invention.

Since the first successful ADMET polymerization,[4] we have actively made efforts to produce novel unsaturated polymers containing a variety of functional groups within the primary structure via metathesis condensation chemistry. To date, Schrock's molybdenum alkylidene (1) (FIG. 1) has been our catalyst of choice for producing such macromolecules; however, Grubbs' ruthenium alkylidene is also capable of producing high molecular weight polymers.[5] The key to both catalysts well-defined nature is their inherit ability to perform metathesis chemistry without the presence of a Lewis acid cocatalyst, thus vinyl addition chemistry is eliminated.[6]

Figure 2:
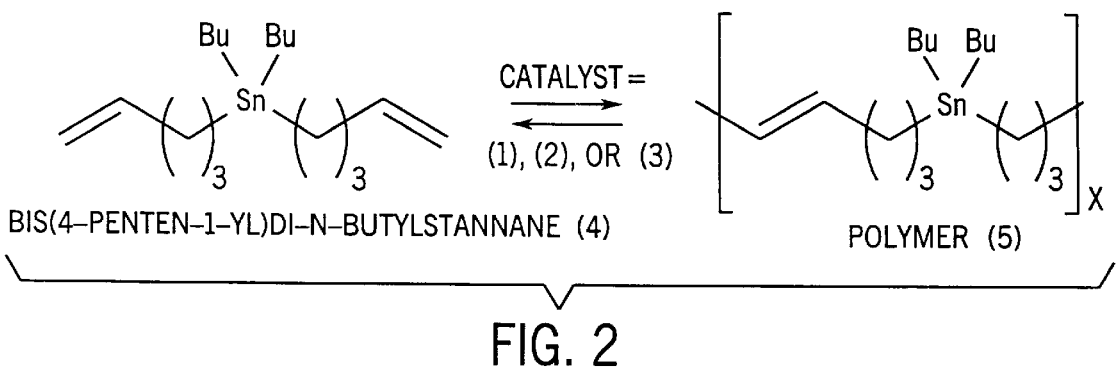
FIG. 2 shows a general ADMET polymerization scheme for the present invention.

Thus, we chose to evaluate the reactivity of bis(4-penten-1-yl)di-n-butylstannane (4) (FIG. 2) in ADMET polymerizations with a well-defined metathesis catalyst (1) (FIG. 1) and with complexes (2) and (3) (FIG. 1) in a classical type metathesis catalytic system. Schrock's molybdenum alkylidene catalyst (1) was chosen for preliminary experiments due to its high reactivity, but we have found that if compound (4) is used in a presence of either complexes (2) or (3), the monomer itself functions as a cocatalyst and produces polymers identical to those obtained from Schrock's well-defined catalyst (1).

Materials.

Mo(CHCMe$_2$Ph) (N-2,6-C$_6$H$_3$-i-Pr$_2$) (OC(Me)$_2$CF$_3$)$_2$[7] (1), W(O)Cl$_2$(O-2,6-C$_6$H$_3$-Br$_2$)$_2$[2] (2), and WCl$_4$(O-2,6-C$_6$H$_3$-Ph$_2$)$_2$[8] (3) were synthesized according to published procedures. 5-Bromo-1-pentene was purchased from either Aldrich Chemical Company or Acros Organics and distilled from CaH$_2$ immediately before use. Di-n-butyltin dichloride was purchased form Acros Organics and used as received. Diethyl ether was distilled from sodium benzophenone ketyl and stored over 4 Å molecular sieves in an inert atmosphere of argon.

$^1$H (300 MHz), $^{13}$C (75 MHz), and $^{119}$Sn (112 MHz) NMR was performed on a Varian VXR-300 MHz superconducting spectrophotometric system. $^1$H and $^{13}$C NMR are referenced to an internal 0.05% w/w TMS standard whereas $^{119}$Sn NMR are referenced to an internal 1% w/w tetramethyltin sample. Elemental analysis was performed by either Robertson Microlit Laboratories, Madison, N.J., or Atlantic Microlab Inc., Norcross, Ga. Gel permeation chromatography (GPC) was performed on a Waters Associates Model 590, chromatograph with three Phenomenex Phenogel columns in series (50,000 Å, 5,000 Å, 500 Å) using both a UV and an RI detector. THF was used as the eluent at a flow rate of 1.0 mL/min, and the instrument was calibrated using polystyrene standards.

Experimental.

Synthesis of Bis(4-penten-1-yl)di-n-butylstannane (4).

The synthesis of bis(4-penten-1-yl)di-n-butylstannane was performed as follows. To 3 equivalents of preformed 4-penten-1-yl magnesium bromide in diethyl ether (1.0M) was charged one equivalent of di-n-bytyltin dichloride in diethyl ether (1.0M) at room temperature over a period of 2 hours and then refluxed for 20 hours. The reaction mixture was then poured into an ice-cold 1M NH$_4$Cl solution. The organic layer was separated, washed with DI H$_2$O, dried over MgSO$_4$, and vacuum distilled under full Schlenk vacuum. The product was then dried over CaH$_2$ for 48 hours under full Schlenk vacuum before being fractionally distilled again yielding bis(4-penten-1-yl)di-n-butylstannane in 83% yield with the following spectral characteristics: $^1$H NMR: δ (ppm)=5.8 (m, 2 H); 4.9 (m, 4H); 2.1 (q, 4 H); 1.6 (m, 4 H): 1.5 (m, 4 H); 1.3 (m, 4 H); 0.9 (m, 14 H). $^{13}$C NMR: δ (ppm)=138.7, 114.4, 38.6, 29.3, 27.4, 26.6, 13.7, 8.8, 8.6. $^{119}$Sn NMR: δ (ppm)=−13.1. Elemental analysis calculated for C$_{18}$H$_{36}$Sn. Calculated: C(58.25%), H(9.78%). Found: C(58.35%), H(9.80%).

ADMET Polymerization of (4).

In an argon purged dry box, the catalyst ((1), (2) or (3), 1 eq) was weighed and placed in a 50 mL round bottomed flask adapted with a Rotoflow valve. The monomer (4) (250 or 500 eq.) was then added to the flask which was in turn sealed and taken to a high vacuum Schlenk line. Vigorous ethylene evolution can be evidenced at room temperature in the case of catalyst (1) during the first 12 h of reaction. After this time, the system is heated to 60° C. In the case of complexes (2) and (3), the reaction is carried out at 90° C. The reaction is stopped by removal of the heat when magnetic agitation becomes impossible. The crude polymer is purified by dissolution in chloroform and subsequent precipitation into methanol or pentane. Anhydrous solvents must be used in the case of the polymer produced with catalysts (2) and (3). All three samples were viscous liquids with the following spectral properties: $^1$H NMR: δ (ppm)= 5.4 (m, br, 2 H); 1.9 (m, br, 4 H); 1.5 (m, 8 H); 1.3 (m, 4 H); 0.9 (m, 14 H) . $^{13}$C NMR; δ (ppm)=103.3 (trans); 129.7 (cis); 37.4 (allylic, trans); 32.2 (allylic, cis); 29.3; 27.4; 27.2; 13.7; 8.8; 8.7. $^{119}$Sn NMR: δ (ppm)=−12.8 (trans, trans); −13.0 (trans, cis); −13.2 (cis, cis). Elemental analysis. Calculated: C(56.00%), H(9.40%) . Found: C(56.23%), H(9.54%).

Results and Discussion.

Polymers containing tin within their structure, either as substituents or within the backbone, are well known, and several methods can be used to produce such macromolecules.[9] Results reported by the authors mentioned above prompted us to investigate the activity of acyclic dienes containing tin moieties within a metathesis polymerization system.

Based on the well-known activity exhibited by tin compounds as cocatalysts for classical metathesis systems, we chose to investigate the aryloxo tungsten (VI) complexes (2), utilized by Feldman et al. in ring closing metathesis (RCM) reactions,[2] and (3), developed by Basset and coworkers,[8] to attempt ADMET condensation chemistry in a classical type system. Preliminary results obtained in our laboratories show that these classical systems can also efficiently catalyze the ADMET polymerization of hydrocarbon dienes. Since the above systems involve either tetraalkyltin or tetralkyllead compounds as cocatalysts, we envisioned the possible reactivity of the bis(alkenyl)tin compound (4) as both the monomer and the cocatalyst. This represents the first metathesis polymerization in which the monomer participates as both the propagating species and the cocatalyst. Due to the highly reactive, well-defined nature of Schrock's alkylidene (1), we synthesized unsaturated polycarbostannanes of a well-defined structure and compared the results obtained from each polymerization system.

The evolution of ethylene is apparent upon contact of monomer (4) with (1). Within 12 hours of reaction, the viscosity reaches a point to which heat must be applied to facilitate the production of high molecular weight polymer. Upon completion of the reaction, the crude polymer was characterized by $^1$H and $^{13}$C NMR. End group analysis of the quantitative $^{13}$C NMR (see FIG. 3) of polymer (5) (FIG. 2) illustrates that high molecular weight polymer has indeed formed with a number average molecular weight of 17,000 g/mol. Integration of the cis (129.7 ppm) and trans (130.8 ppm) olefin resonances yields a cis:trans ratio of 21:79 which is typical of ADMET polymerizations. GPC analysis computes a molecular weight of approximately 36,000 g/mol; however, this number is a direct reflection of the difference in hydrodynamic volume between the polycarbostannane sample and the polystyrene standard.

Figure 4:
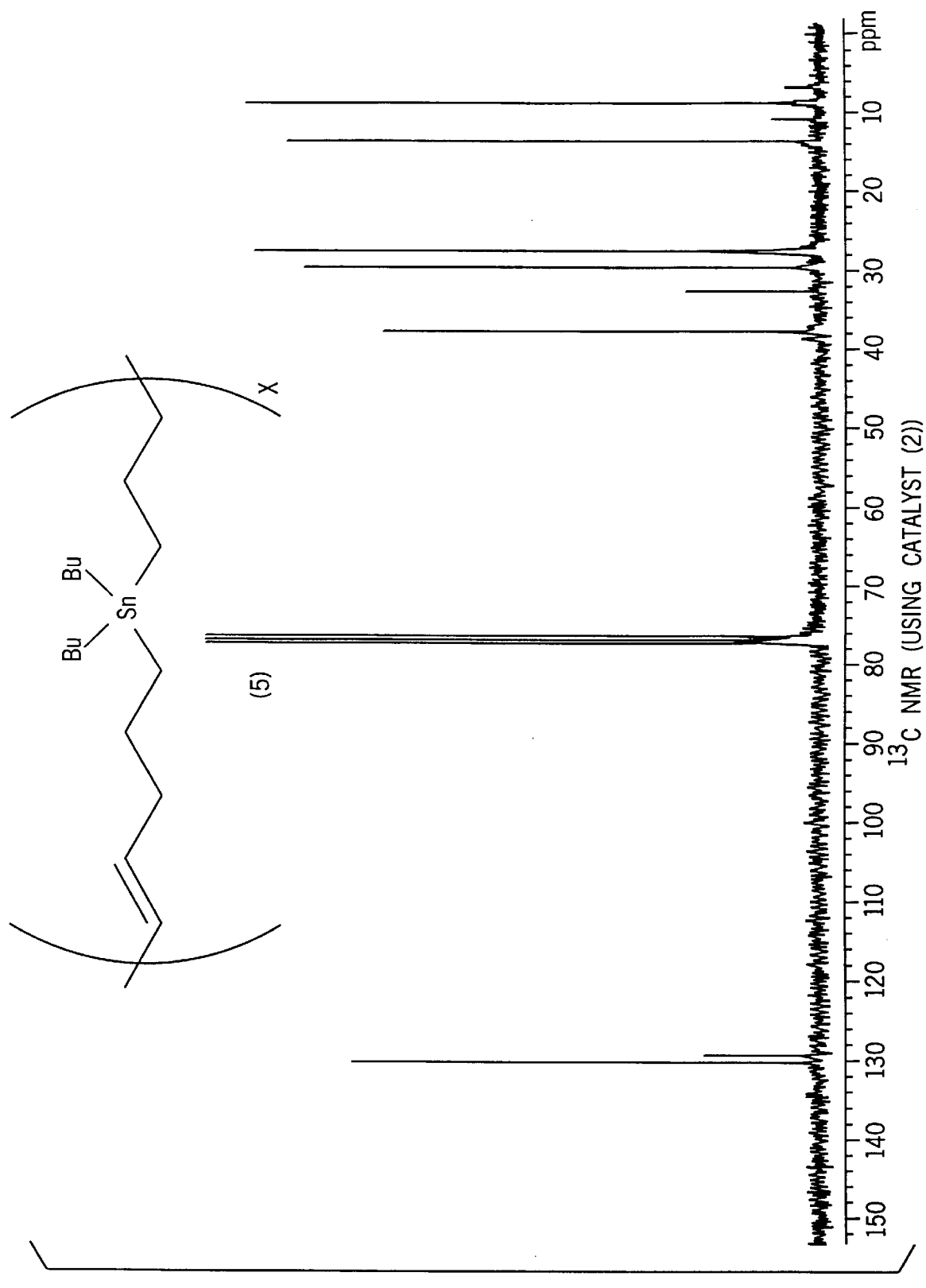

The polymerization of (4) with either complex (2) or (3) also produces high molecular weight polymer (5) (see FIGS. 4 and 5). The reaction requires higher temperatures to facilitate the transmetallation-elimination reaction that occurs between the tin monomer and complex (2), leading to the formation of the active metathetic species.[1] Our observation that gelation occurs upon contact of the product polymers with moisture, supports the work of Basset in that the hydrolysis of a Sn-Cl bond (which is formed in the initial transmetallation step between the tin monomer and complex (2) or (3)) must be occurring to produce a crosslinked polymer while no gelation is observed with (5) produced from (1), or when the polymer is synthesized via the complexes (2) or (3) and are worked up under anhydrous conditions. The number average molecular weights obtained from $^1$H and quantitative $^{13}$C NMR analysis is about 9,300 g/mol for the polymerization catalyzed by (2) and about 16,0900 g/mol for the polymer synthesized using complex (3), while GPC reveals Mn=17,000 and Mn=30,000 g/mol respectively.

The incorporation of the metal is clearly evidenced by the three resonances observed in the $^{119}$Sn NMR spectrum of polymer (5) produced using catalyst (1) (see FIG. 6), assigned to the metal in three different environments arising from the geometry of the double bonds by which it is surrounded (trans-trans, trans-cis and cis-cis). Based on the intensity of the corresponding signals in the quantitative $^{13}$C NMR, the cis:trans ratio was determined to be 21:79 for polymer (5) synthesized using catalyst(1), while the intensity of the three signals in the $^{119}$Sn NMR was found to be 65:30:5, a value in good agreement with a distribution of 64:32:4 calculated from the $^{13}$C NMR data. Polymer (5) synthesized using catalyst (2) displayed a cis:trans ratio of 19:81 with a trans-trans:trans-cis:cis-cis ratio from $^{119}$Sn NMR of 64:32:5. Catalyst (3) produced polymer (5) with a trans-trans:trans-cis:cis-cis ratio of 59:35:6, and the total cis:trans ratio as determined by quantitative $^{13}$C NMR is 26:74.

CONCLUSIONS

We have shown that the synthesis of an unsaturated polycarbostannane from bis(4-penten-1-yl)di-n-butylstannane via ADMET polymerization can be accomplished by the use of either a well-defined alkylidene or classical catalytic systems based on tungsten aryloxo complexes. In the latter case, these complexes are converted into an active catalyst by activation with the monomer itself.

Thus, it can be seen that the present invention provides unsaturated polycarbostannanes via metathesis chemistry. It should be understood that unsaturated polymers containing a variety of metals along the polymer backbone can also be synthesized using the method of the present invention and various bis(alkenyl) metal monomers.

For example, metals such as Ge, Pb, Hg, Ni, Pd, Pt, Cr, Fe, Co, Cu, and Zn can be substituted for tin in the bis(alkenyl) monomer. Further, other bis(alkenyl)dialkylstannanes may be used as monomers to make other unsaturated polycarbostannanes according to the present invention. Preferably, the alkenyl group of the bis(alkenyl) metal monomer has 2–30 carbons, more preferably 3–6 carbons.

With regard to $R_1$ and $R_2$, when alkyl is selected the alkyl preferably has one to six carbons, when aromatic is selected the aromatic preferably has one to three rings, and when alkenyl is selected the alkenyl preferably has two to six carbons. It should be noted that when $R_1$ and/or $R_2$ are/is an alkenyl group, the polymer would assume interesting characteristics due to branching and cross-linking. Such branched and cross-linked polymers would have advantageous applications as coatings for use in paints, for example.

It should also be understood that the present invention includes polymers made from unbalanced acyclic dienes (where n≠p). Such polymers would be especially useful as coatings because of their enhanced durability.

It should be further understood that a suitable carrier for the polymer of the present invention in antibacterial, antifungal compositions of the above kind can include solvents or other polymers. Also, the carrier can include solids such as titanium dioxide. It will also be appreciated that the polymer of the present invention could be applied to a surface (e.g., a ship hull) by combining the monomer and catalyst via a spray/mixing nozzle. The polymer would then be formed and cured in situ.

The ADMET chemical synthesis of the polymers of the present invention would follow directly from that shown for the exemplary polymer above. The synthesis of the starting monomers would be according to standard organic techniques.

The claims should therefore be looked to in order to assess the full scope of the invention.

(1) Quignard, F.; Leconte, M.; Basset, J. M. J. *Mol. Cat.* 1986, 36, 13.

(2) Nugent, W. A.; Feldman, J.; Calabrese, J. C. J. *Am. Chem. Soc.* 1995, 117, 8992.

(3) Nubel, P. O.; Lutman, C. A.; Yokelson, H. B. *Macromolecules.* 1994, 27, 7000.

(4) Wagener, K. B.; Boncella, J. M.; Nel, J. G. *Macromolecules.* 1991, 24, 1991.

(5) Brzezinska, K.; Wolfe, P. S.; Watson, M.D.; Wagener, K. B.; *Macromol. Chem. Phys.* 1996, 197, 2065.

(6) Wagener, K. B.; Boncella, J. M.; Nel, J. G.; Duttweiler, R. P.; Hillmyer, M. A. *Makromol. Chem.* 1990, 191, 365.

(7) Schrock, R. R.; Murdzek, G. C.; Bazan, J. R.; DiMare, M.; O'Regan, M. J. *Am. Chem. Soc.* 1990, 112, 3875.

(8) Quignard, Francoise; Leconte, Michel; Basset, Jean-Marie; Hsu, Leh-Yeh; Alexander, John J.; Shore, Sheldon G. *Inorg. Chem.* 1987, 26, 4272.

(9) Pomogailo, Anatoly D.; Savost'yanov, Vladimir S. "Synthesis and Polymerization of Metal-Containing Polymers". CRC Press, Inc.; Boca Raton, Fla. 1994. 164 p.

We claim:

1. An organometallic polymer having the following moiety:

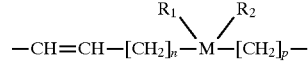

wherein:
(a) n=0–30;
(b) p=0–30;
(c) $R_1$ and $R_2$ are independently selected from the group consisting of H, an alkyl group having 30 or fewer carbons, an alkyl group having 30 or fewer carbons, and an aromatic group having one to ten rings; and
(d) M is a metal selected from the group consisting of Sn, Ge, Pb, Hg, Ni, Pd, Pt, Cr, Fe, Co, Cu, and Zn.

2. The polymer of claim 1, wherein M is Sn.

3. The polymer of claim 2, wherein $R_1$ and $R_2$ are n-butyl, n is 3, and p is 3.

4. An antibacterial, antifungal composition comprising the polymer of claim 1 and a suitable carrier.

5. An antibacterial, antifungal composition comprising the polymer of claim 2 and a suitable carrier.

6. An antibacterial, antifungal composition comprising the polymer of claim 3 and a suitable carrier.

7. A method of making an organometallic polymer comprising the steps of:

adding a bis(alkyl) metal monomer to a suitable catalyst, but without the presence of a co-catalyst;

reacting the monomer under vacuum at a temperature between room temperature and 90° C. to form a crude mixture of a polymer having the moiety

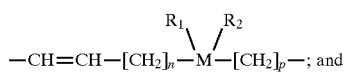

purifying the polymer from the crude mixture;
wherein:
(a) n=0–30;
(b) p=0–30;
(c) $R_1$ and $R_2$ are independently selected from the group consisting of H, an alkyl group having 30 or fewer carbons, an alkyl group having 30 or fewer carbons, and an aromatic group having one to ten rings; and
(d) M is a metal selected from the group consisting of Sn, Ge, Pb, Hg, Ni, Pd, Pt, Cr, Fe, Co, Cu, and Zn.

8. The method of claim 7, wherein the catalyst is selected from the group of molybdenum alkylidene and tungsten aryloxo complexes.

9. The method of claim 7, wherein M is Sn.

10. The method of claim 9, wherein $R_1$ and $R_2$ are n-butyl, n is 3, and p is 3.

11. A method of controlling the growth of organisms, comprising:
    contacting the organisms with a compound according to claim 1 in an amount effective for the control of the growth of the organisms.

12. A method of controlling the growth of organisms, comprising:
    contacting the organisms with a compound according to claim 2 in an amount effective for the control of the growth of the organisms.

13. A method of controlling the growth of organisms, comprising:
    contacting the organisms with a compound according to claim 3 in an amount effective for the control of the growth of the organisms.

* * * * *